(12) United States Patent
Bednarek

(10) Patent No.: US 7,335,723 B2
(45) Date of Patent: Feb. 26, 2008

(54) MELANIN-CONCENTRATING HORMONE ANTAGONISTS

(75) Inventor: Maria A. Bednarek, Colonia, NJ (US)

(73) Assignee: Merck & Co., Inc., Rahway, NJ (US)

( * ) Notice: Subject to any disclaimer, the term of this patent is extended or adjusted under 35 U.S.C. 154(b) by 360 days.

(21) Appl. No.: 10/485,682

(22) PCT Filed: Aug. 2, 2002

(86) PCT No.: PCT/US02/26796

§ 371 (c)(1),
(2), (4) Date: Feb. 3, 2004

(87) PCT Pub. No.: WO03/013574

PCT Pub. Date: Feb. 20, 2003

(65) Prior Publication Data

US 2004/0254338 A1 Dec. 16, 2004

Related U.S. Application Data

(60) Provisional application No. 60/310,928, filed on Aug. 8, 2001.

(51) Int. Cl.
A61K 38/12 (2006.01)
A61K 38/00 (2006.01)
A01N 37/18 (2006.01)
(52) U.S. Cl. .............. 530/317; 514/2; 514/9; 530/311
(58) Field of Classification Search ............ 530/317, 530/311; 514/9
See application file for complete search history.

(56) References Cited

U.S. PATENT DOCUMENTS

| 5,049,655 A | 9/1991 | Vaughan et al. |
| 5,849,708 A | 12/1998 | Maratos-Flier |

FOREIGN PATENT DOCUMENTS

| WO | WO90/11295 | 10/1990 |
| WO | WO01/57070 | 8/2001 |
| WO | WO02/097037 | 12/2002 |
| WO | WO03/060091 | 7/2003 |

OTHER PUBLICATIONS

Bednarek et al. Short segment of human melanin-concentrating hormone that is sufficient for full activation of human melanin-concentrating hormone receptors 1 and 2. Biochemistry. Aug. 7, 2001;40(31):9379-86.*
Audinot et al. Structure-activity relationship studies of melanin-concentrating hormone (MCH)-related peptide ligands at SLC-1, the human MCH receptor. J Biol Chem. Apr. 27, 2001;276(17):13554-62. Epub Jan. 18, 2001.*
MacDonald et al. Molecular characterization of the melanin-concentrating hormone/receptor complex: identification of critical residues involved in binding and activation. Mol Pharmacol. Jul. 2000;58(1):217-25.*
Chimania et al. Predominant GABA-B mediated dispersion of the isolated web melanophores of the the indian bull frog, *Rana tigerina* (Daud.). Indian J Exp Biol. May 1995;27(5): 241-4.*
Schwartz et al. ("Rats Lighten Up With MCH Antagonist", Nature Medicine 8, 779-781 (2002); http://www.nature.com/nm/journal/v8/n8/full/nm0802-779.html).*
An, S. et al. "Identification and characterization of a melanin-concentrating hormone receptor", PNAS, 2001, vol. 98, pp. 7576-7581.
Audinot, V. et al. "Structure-Activity Relationship Studies of Melanin-concentrating Hormone (MCH)-related Peptide Ligands at SLC-1, the Human MCH Receptor", The Journal of Biological Chemistry, 2001, vol. 276, pp. 13554-13562.
Bachner, D. et al. "Identification of melanin concentrating hormone (MCH) as the natural ligand for the orphan somatostatin-like receptor 1 (SLC-1)", FEBS Letters, 1999, vol. 457, pp. 522-524.
Baker, B. et al. "Structure-Activity Studies With Fragments and Analogues of Salmonid Melanin-Concentrating Hormone", Peptides, 1990, vol. 11, pp. 1103-1108.
Bednarek, M. et al. "Short Segment of Human Melanin-Concentrating Hormone That Is Sufficient for Full Activation of Human Melanin-Concentrating Hormone Receptors 1 and 2", Biochemistry, 2001, vol. 40, pp. 9379-9386.
Bednarek, M. et al. "Synthesis and Biological Evaluation in Vitro of a Selective, High Potency Peptide Agonist of Human Melanin-concentrating Hormone Action at Human Melanin-concentrating Hormone Receptor 1", The Journal of Biological Chemistry, 2002, vol. 277, pp. 13821-13826.
Bednarek, M. et al. "Synthesis and Biological Evaluation in Vitro of Selective, High Affinity Peptide Antagonists of Human Melanin-Concentrating Hormone Action at Human Melanin-Concentrating Hormone Receptor 1", Biochemistry, 2002, vol. 41, pp. 6383-6390.
Breton, C. et al. "Isolation and characterization of the human melanin-concentrating hormone gene and a variant gene", Molecular Brain Research, 1993, vol. 18, pp. 297-310.
Chambers, J. et al. "Melanin-concentrating hormone is the cognate ligand for the orphan G-protein-coupled receptor SLC-1", Nature, 1999, vol. 400, pp. 261-265.
Chimania, S. et al. "Predominant GABAB Mediated Dispersion of the Isolated Web Melanophores of the Indian Bull Frog, *Rana tigerina* (Daud.)", Indian Journal of Pharmacology, 1995, vol. 27, pp. 241-244.
Drozdz, R. et al. "D-(p-Benzoylphenylalanine)13, Tyrosine19)-Melanin-concentrating Hormone, a Potent Analogue for MCH Receptor Crosslinking", Journal of Peptide Science, 1999, vol. 5, pp. 234-242.

(Continued)

Primary Examiner—Cecilia J. Tsang
Assistant Examiner—Maury Audet
(74) Attorney, Agent, or Firm—Catherine D. Fitch; Sheldon O. Heber

(57) ABSTRACT

The present invention features MCH antagonists active at the MCH-1R. The antagonists are optionally modified peptides able to inhibit the effect of MCH at MCH-1R. MCH antagonists have a variety of uses including being used as a research tool and being used to achieve a beneficial effect in a subject.

14 Claims, No Drawings

OTHER PUBLICATIONS

Drozdz, R. et al. "Melanin-concentrating hormone binding to mouse melanoma cells in vitro", FEBS Letters, 1995, vol. 359, pp. 199-202.

Erickson, J. et al. "Sensitivity to leptin and susceptibility to seizures of mice lacking neuropeptide Y", Nature, 1996, vol. 381, pp. 415-418.

Flier, J. et al. "Obesity and the Hypothalamus: Novel Peptides for New Pathways", Cell, 1998, vol. 92, pp. 437-440.

Hawes, B. et al. "The Melanin-Concentrating Hormone Receptor Couples to Multiple G Proteins to Activate Diverse Intracellular Signaling Pathways", Endocrinology, 2000, vol. 141, pp. 4524-4532.

Hintermann, E. et al. "Synthesis and Characterization of New Radioligands for the Mammalian Melanin-Concentrating Hormone (MCH) Receptor", Journal of Receptor & Signal Transduction Research, 1999, vol. 19, pp. 411-422.

Kawauchi, H. et al. "Characterization of melanin-concentrating hormone in chum salmon pituitaries", Nature, 1983, vol. 305, pp. 321-323.

Knigge, K. et al. "Melanotropic Peptides in the Mammalian Brain: The Melanin-Concentrating Hormone", Peptides, 1996, vol. 17, pp. 1063-1073.

Lebl, M. et al. "Melanin Concentrating Hormone Analogues: Contraction of the Cyclic Structure. 1. Angonist Activity", Journal of Medicinal Chemistry, 1988, vol. 31, pp. 949-954.

MacDonald, D. et al. "Molecular Characterization of the Melanin-Concentrating Hormone/Receptor Complex: Identification of Critical Residues Involved in Binding and Activation", Molecular Pharmacology, 2000, vol. 58, pp. 217-225.

Nahon, J. "The Melanin-Concentrating Hormone: From the Peptide to the Gene", Critical Reviews in Neurobiology, 1994, vol. 8, pp. 221-262.

Presse, F. et al. "Structure of the Human Melanin Concentrating Hormone mRNA", Molecular Endocrinology, 1990, vol. 4, pp. 632-637.

Qu, D. et al. "A role for the melanin-concentrating hormone in the central regulation of feeding behaviour", Nature, 1996, vol. 380, pp. 243-247.

Sailer, A. et al. Identification and characterization of a second melanin-concentrating hormone receptor, MCH-2R, PNAS, 2001, vol. 98, pp. 7564-7569.

Saito, Y. et al. "Melanin-concentrating Hormone Receptor: An Orphan Receptor Fits the Key", Trends in Endocrinology and Metabolism, 2000, vol. 11, pp. 299-303.

Saito, Y. et al. "Molecular characterization of the melanin-concentrating-hormone receptor", Nature, 1999, vol. 400, pp. 265-269.

Shimada, M. et al. "Mice lacking melanin-concentrating hormone are hypophagic and lean", Nature, 1998, vol. 396, pp. 670-674.

Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.

Vaughan, J. et al. "Characterization of Melanin-Concentrating Hormone from Rat Hypothalamus", Endocrinology, 1989, vol. 125, pp. 1660-1665.

Wang, S. et al. "Identification and Pharmacological Characterization of a Novel Human Melanin-concentrating Hormone Receptor, MCH-R2", The Journal of Biological Chemistry, 2001, vol. 276, pp. 34664-34670.

* cited by examiner

MELANIN-CONCENTRATING HORMONE ANTAGONISTS

CROSS-REFERENCE TO RELATED APPLICATIONS

The present application claims priority to provisional application U.S. Ser. No. 60/310,928, filed Aug. 8, 2001, hereby incorporated by reference herein.

BACKGROUND OF THE INVENTION

Neuropeptides present in the hypothalamus play a major role in mediating the control of body weight. (Flier, et al., 1998. *Cell*, 92, 437-440.) Melanin-concentrating hormone (MCH) produced in mammals is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol.* 4, 632-637; Vaughan, et al., U.S. Pat. No. 5,049,655; and Vaughan, et al., 1989. *Endocrinology* 125, 1660-1665.) MCH was first identified in salmon pituitary, and in fish MCH affects melanin aggregation thus affecting skin pigmentation. In trout and eels MCH has also been shown to be involved in stress induced or CRF-stimulated ACTH release. (Kawauchi, et al., 1983. *Nature* 305, 321-323.)

In humans two genes encoding MCH have been identified that are expressed in the brain. (Breton, et al., 1993. *Mol. Brain Res.* 18, 297-310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063-1073.)

Pharmacological and genetic evidence suggest that the primary mode of MCH action is to promote feeding (orexigenic). MCH mRNA is up regulated in fasted mice and rats, in the ob/ob mouse and in mice with targeted disruption in the gene for neuropeptide Y (NPY). (Qu, et al., 1996. *Nature* 380, 243-247 and Erickson, et al., 1996. *Nature* 381, 415-418.) Injection of MCH centrally (ICV) stimulates food intake and MCH antagonizes the hypophagic effects seen with α melanocyte stimulating hormone (αMSH). (Qu, et al., 1996. *Nature* 380, 243-247.) MCH deficient mice are lean, hypophagic and have increased metabolic rate. (Shimada, et al., 1998. *Nature* 396, 670-673.) The administration of MCH has been indicated to be useful for promoting eating, appetite or the gain or maintenance of weight. (Maratos-Flier, U.S. Pat. No. 5,849,708.)

MCH action is not limited to modulation of food intake as effects on the hypothalamic-pituitary-axis have been reported. (Nahon, 1994. *Critical Rev. in Neurobiol.* 8, 221-262.) MCH may be involved in the body response to stress as MCH can modulate the stress-induced release of CRF from the hypothalamus and ACTH from the pituitary. In addition, MCH neuronal systems may be involved in reproductive or maternal function.

MCH can bind to at least two different receptors: MCH-1R and MCH-2R. (Chambers, et al., 1999. *Nature* 400, 261-265; Saito, et al., 1999. *Nature* 400, 265-269; Bächner, et al., 1999. *FEBS Letters* 457:522-524; Shimomura, et al., 1999. *Biochemical and Biophysical Research Communications* 261, 622-626; Sailer, et al., *Proc. Natl. Acad. Sci.* 98:7564-7569, 2001.) The amino acid identity between MCH-2R and MCH-1R is about 38%. (Sailer, et al., *Proc. Natl. Acad. Sci.* 98:7564-7569, 2001.)

SUMMARY OF THE INVENTION

The present invention features MCH antagonists active at the MCH-1R. The antagonists are optionally modified peptides able to inhibit the effect of MCH at MCH-1R. MCH antagonists have a variety of uses including being used as a research tool and being used to achieve a beneficial effect in a subject.

Different combinations of alterations to a mammalian MCH are identified herein as useful for producing an MCH antagonist. Examples of such alterations include a truncated mammalian MCH containing positions 6 to 16 where positions 14 and 15 are either 5-aminovaleric acid, gamma-aminobutyric acid, or β-alanine, in combination with either or both (1) positions 9 and 10 being 5-aminovaleric acid and (2) position 6 being either 5-guanidinovaleric acid or D-arginine.

The identification of different alterations to a truncated mammalian MCH that are useful for obtaining an MCH antagonist provides guidance that can be used to obtain additional MCH antagonists. The additional MCH antagonists can be of varying sizes and can contain different types of alterations in different positions. The ability of a compound to act as an antagonist can be evaluated using techniques well known in the art.

Thus, a first aspect of the present invention describes a MCH antagonist. The MCH antagonist is an optionally modified cyclic peptide having either a disulfide or lactam ring. Structure I illustrates the disulfide ring while Structures II and III illustrate a lactam ring.

Structure I is as follows:

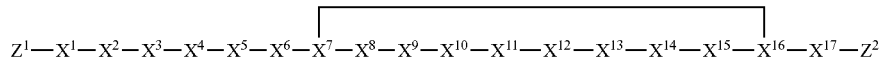

wherein $X^1$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or norleucine, or a derivative thereof;

$X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^6$ is an optionally present amino acid that, if present is either arginine, alanine, leucine, glycine, lysine, proline, asparagine, serine, histidine, nitroarginine, homoarginine, citrulline, homocitrulline, norleucine, D-arginine, des-amino-arginine, 4-guanidinobutyric acid, 3-guanidino propionic acid, guanidinoacetic acid, or 3-guanidino propionic acid, or a derivative thereof;

$X^7$ is either cysteine, homocysteine, penicillamine, or D-cysteine, or a derivative thereof;

$X^8$ is either methionine, norleucine, leucine, isoleucine, valine, methioninesulfoxide, gamma-aminobutyric acid, or methioninesulfone, or a derivative thereof;

$X^9$ is either leucine, isoleucine, valine, alanine, methionine, 5-aminopentanoic acid, D-norleucine, 5-aminovaleric acid, gamma-aminobutyric acid, or β-alanine, or a derivative thereof;

$X^{10}$ is either glycine, alanine, leucine, norleucine, cyclohexylalanine, 5-aminopentanoic acid, asparagine, serine, sarcosine, isobutyric, D-norleucine, 5-aminovaleric acid, gamma-aminobutyric acid, or β-alanine, or a derivative thereof;

$X^{11}$ is either arginine, lysine, citrulline, histidine, or nitroarginine, or a derivative thereof;

$X^{12}$ is either valine, leucine, isoleucine, alanine, or methionine, or a derivative thereof;

$X^{13}$ is either phenylalanine, tyrosine, D-(p-benzoylphenylalanine), tryptophan, (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br; or a derivative thereof;

$X^{14}$ is either 5-aminovaleric acid, gamma-aminobutyric acid, β-alanine, or cis-4-amino-1-cyclohexancarboxylic acid;

$X^{15}$ is either 5-aminovaleric acid, gamma-aminobutyric acid, β-alanine, or cis-4-amino-1-cyclohexancarboxylic acid;

$X^{16}$ is either cysteine, homocysteine, or penicillamine, or a derivative thereof;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$Z^1$ is an optionally present protecting group that, if present, is covalently joined to the N-terminal amino group;

$Z^2$ is an optionally present protecting group that, if present, is covalently joined to the C-terminal carboxy group;

provided that one or both of the following applies:

$X^9$ and $X^{10}$ are each independently selected from the group consisting of: 5-aminovaleric acid, gamma-aminobutyric acid, β-alanine, and cis-4-amino-1-cyclohexancarboxylic acid; and $X^6$ is either 5-guanidinovaleric acid, D-arginine, 4-guanidinobutyric acid, 3-guanidino propionic acid, guanidinoacetic acid or 3-guanidino propionic acid;

or a labeled derivative of said peptide;

or a pharmaceutically acceptable salt of said peptide or of said labeled derivative.

Structure II is as follows:

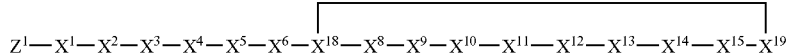

wherein $X^1$, $X^2$, $X^3$, $X^4$, $X^5$, $X^6$, $X^8$, $X^9$, $X^{10}$, $X^{11}$, $X^{12}$, $X^{13}$, $X^{14}$, $X^{15}$, and $Z^1$ is as described for Structure I; $X^{18}$ is a α,ω-di-amino-carboxylic acid having the following structure:

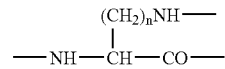

where n is either 1, 2, 3, 4, or 5; and $X^{19}$ is a ω-carboxy-α-amino acid, such as aspartic acid, glutamic acid, or adipic acid. The ω-amino group of the $X^{18}$ α,ω-di-amino-carboxylic acid is coupled to the carboxy group of the $X^{19}$ amino acid.

Structure III is as follows:

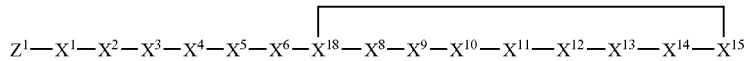

wherein $X^1$, $X^2$, $X^3$, $X^4$, $X^5$, $X^6$, $X^8$, $X^9$, $X^{10}$, $X^{11}$, $X^{12}$, $X^{13}$, $X^{14}$, $X^{15}$, $X^{18}$ and $Z^1$ is as described for Structure II and the ω-amino group of the $X^{18}$ α,ω-di-amino-carboxylic acid is coupled to the carboxy group at position 15.

Reference to "amino acid" includes naturally occurring amino acids and altered amino acids. Unless otherwise stated, those amino acids with a chiral center are provided in the L-enantiomer. Reference to "a derivative thereof" refers to the corresponding D-amino acid, N-alkyl-amino acid and β-amino acid.

Another aspect of the present invention describes a method of inhibiting MCH-1R activity in a subject. The method comprises the step of administering to the subject an effective amount of an MCH antagonist.

Reference to "effective" amount indicates an amount sufficient to achieve a desired effect. In this aspect of the invention, the effective amount is sufficient to inhibit MCH-1R activity.

Another aspect of the present invention describes a method of treating a subject to achieve a weight loss or to maintain weight. The method comprises the step of administering to the subject an effective amount of an MCH antagonist.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

MCH-1R can reduce to a detectable extent one or more activities caused by MCH at the MCH-1R.

MCH antagonists can be administered to a subject. A "subject" refers to a mammal including, for example, a human, a rat, a mouse, or a farm animal. Reference to subject does not necessarily indicate the presence of a disease or disorder. The term subject includes, for example, mammals being dosed with a MCH antagonist as part of an experiment, mammals being treated to help alleviate a disease or disorder, and mammals being treated prophylactically.

MCH antagonists can be used to achieve a beneficial effect in a patient. For example, a MCH antagonist can be used to facilitate weight loss, appetite decrease, weight maintenance, cancer (e.g., colon or breast) treatment, pain reduction, stress reduction and/or treatment of sexual dysfunction.

MCH Antagonists

MCH antagonists described include the optionally modified peptides of Structure I, II, or III. Structure I is as follows:

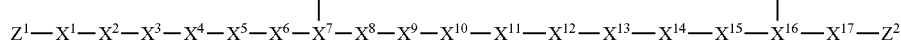

DETAILED DESCRIPTION OF THE INVENTION

Different alterations to mammalian MCH are identified as providing for MCH antagonist activity. Such alterations illustrate the types of changes that can be made to MCH or an MCH-like compound to produce an MCH antagonist.

Preferred MCH antagonists are about 11 amino acids in length. The smaller size of an MCH antagonist offers advantages over a longer-length MCH antagonist such as ease of synthesis and/or increased solubility in physiological buffers.

Preferred MCH antagonists can significantly inhibit MCH-1R activity. Significant inhibition of MCH-1R activity can be evaluated by measuring the antagonist $IC_{50}$ in an assay involving the MCH-1R, and an MCH-1R agonist that activates the receptor. In different embodiments, the MCH antagonist has an $IC_{50}$ value less than about 50 nM, less than about 10 nM, and less than about 5 nM, in an assay measuring functional activity. An example of such an assay is provided in the Examples below.

An embodiment of the present invention describes MCH-1R antagonists selectively active at the MCH-1R over the MCH-2R. Preferred selective antagonists significantly inhibit MCH-1R while not significantly inhibiting MCH-2R activity. The ability of a compound to inhibit MCH-2R activity can be directly measured by evaluating antagonist activity. Alternatively, measuring MCH-2R agonist activity can be used to determine if a compound may act as an MCH antagonist at the MCH-2R.

MCH antagonists have a variety of different uses including being used as a research tool and being used therapeutically. Examples of research tool applications include examining the role or effect of MCH, and examining the role or effects of MCH antagonists.

MCH antagonists can be used to inhibit MCH-1R activity in vitro or in vivo. Reference to "inhibit" or "inhibiting" indicates a detectable decrease. Inhibit and inhibiting do not require the complete absence of an activity. For example, an MCH antagonist able to inhibit the effect of MCH at wherein $X^1$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^1$ if present is aspartic acid or glutamic acid; more preferably, $X^1$ if present is aspartic acid; and more preferably, $X^1$ is not present;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^2$ if present is phenylalanine or tyrosine; more preferably, $X^2$ if present is phenylalanine; and more preferably, $X^2$ is not present;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^3$ if present is aspartic acid or glutamic acid; more preferably, $X^3$ if present is aspartic acid; and more preferably, $X^3$ is not present;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or norleucine, or a derivative thereof; preferably, $X^4$ if present is methionine, leucine, isoleucine, valine, alanine or norleucine; more preferably, $X^4$ if present is methionine; and more preferably, $X^4$ is not present;

$X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^5$ if present is leucine, methionine, isoleucine, valine or alanine; more preferably, $X^5$ if present is leucine; and more preferably, $X^5$ is not present;

$X^6$ is an optionally present amino acid that, if present is either arginine, alanine, leucine, glycine, lysine, proline, asparagine, serine, histidine, nitroarginine, homoarginine, citrulline, homocitrulline, norleucine, D-arginine, des-amino-arginine, 4-guanidinobutyric acid, 3-guanidino propionic acid, guanidinoacetic acid, or 3-guanidino propionic acid, or a derivative thereof; preferably $X^6$ is either 5-guanidinovaleric acid, D-arginine, 4-guanidinobutyric acid, 3-guanidino propionic acid, guanidinoacetic acid or 3-guanidino propionic acid; more preferably D-arginine, des-amino-arginine; more preferably $X^6$ is des-amino-arginine;

$X^7$ is either cysteine, homocysteine, penicillamine, or D-cysteine, or a derivative thereof; preferably, $X^7$ is cysteine;

$X^8$ is either methionine, norleucine, leucine, isoleucine, valine, methioninesulfoxide, gamma-aminobutyric acid, or methioninesulfone, or a derivative thereof; preferably, $X^8$ is methionine or norleucine;

$X^9$ is either leucine, isoleucine, valine, alanine, methionine, 5-aminopentanoic acid, D-norleucine, 5-aminovaleric acid, gamma-aminobutyric acid, or β-alanine, or a derivative thereof; preferably, $X^9$ is leucine, 5-aminovaleric acid, gamma-aminobutyric acid, or β-alanine; more preferably $X^9$ is leucine or 5-aminovaleric acid; more preferably $X^9$ is 5-aminovaleric acid;

$X^{10}$ is either glycine, alanine, leucine, norleucine, cyclohexylalanine, 5-aminopentanoic acid, asparagine, serine, sarcosine, isobutyric, D-norleucine, 5-aminovaleric acid, gamma-aminobutyric acid, or β-alanine, or a derivative thereof; preferably, $X^{10}$ is either glycine, D-norleucine, or 5-aminovaleric acid; more preferably $X^{10}$ is 5-aminovaleric acid;

$X^{11}$ is either arginine, lysine, citrulline, histidine, or nitroarginine, or a derivative thereof; preferably, $X^{11}$ is arginine;

$X^{12}$ is either valine, leucine, isoleucine, alanine, or methionine, or a derivative thereof; preferably, $X^{12}$ is valine or alanine;

$X^{13}$ is either phenylalanine, tyrosine, D-(p-benzoylphenylalanine), tryptophan, (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br; or a derivative thereof; preferably, $X^{13}$ is phenylalanine, (2')napthylalanine, p-fluoro-phenylalanine, tyrosine, or cyclohexylalanine; more preferably $X^{13}$ is tyrosine;

$X^{14}$ is either 5-aminovaleric acid, gamma-aminobutyric acid, β-alanine, or cis-4-amino-1-cyclohexancarboxylic acid; preferably, $X^{14}$ is either 5-aminovaleric acid, gamma-aminobutyric acid, or β-alanine;

$X^{15}$ is either 5-aminovaleric acid, gamma-aminobutyric acid, β-alanine, or cis-4-amino-1-cyclohexancarboxylic acid; preferably, $X^{15}$ is either 5-aminovaleric acid, gamma-aminobutyric acid, or β-alanine;

$X^{16}$ is either cysteine, homocysteine, or penicillamine, or a derivative thereof; preferably, $X^{16}$ is cysteine or D-cysteine;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^{17}$ if present is tyrosine or tryptophan; more preferably $X^{17}$ is not present;

$Z^1$ is an optionally present protecting group that, if present, is covalently joined to the N-terminal amino group;

$Z^2$ is an optionally present protecting group that, if present, is covalently joined to the C-terminal carboxy group;

or a labeled derivative of said peptide;

or a pharmaceutically acceptable salt of said peptide or of said labeled derivative.

Structure II is as follows:

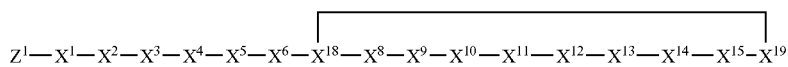

wherein $X^1$, $X^2$, $X^3$, $X^4$, $X^5$, $X^6$, $X^8$, $X^9$, $X^{10}$, $X^{11}$, $X^{12}$, $X^{13}$, $X^{14}$, $X^{15}$, and $Z^1$ is as described for Structure I including the different embodiments; $X^{18}$ is a α,ω-di-amino-carboxylic acid having the following structure:

where n is either 1, 2, 3, 4, or 5; and $X^{19}$ is a ω-carboxy-α-amino acid, such as aspartic acid, glutamic acid, or adipic acid. The ω-amino group of the $X^{18}$ α,ω-di-amino-carboxylic acid is coupled to the ω-carboxy group of the $X^{19}$ amino acid.

Structure III is as follows:

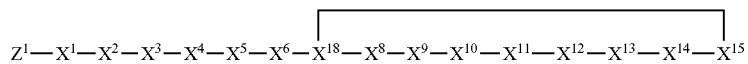

wherein $X^1$, $X^2$, $X^3$, $X^4$, $X^5$, $X^6$, $X^8$, $X^9$, $X^{10}$, $X^{11}$, $X^{12}$, $X^{13}$, $X^{14}$, $X^{15}$, $X^{18}$, and $Z^1$ is as described for Structure II including the different embodiments and the $X^{18}$ α,ω-diamino-carboxylic acid is coupled to the carboxy group at position 15.

The present invention is meant to comprehend diastereomers as well as their racemic and resolved enantiomerically pure forms. MCH antagonists can contain D-amino acids, L-amino acids or a combination thereof. Preferably, amino acids present in a MCH antagonist are the L-enantiomer.

More preferred embodiments contain preferred (or more preferred) groups in each of the different locations. In different embodiments, MCH antagonists contain a preferred (or more preferred) group at one or more different locations; $X^9$ and $X^{10}$ are the same group; and/or $X^{14}$ and $X^{15}$ are the same group.

A protecting group covalently joined to the N-terminal amino group reduces the reactivity of the amino terminus under in vivo conditions. Amino protecting groups include optionally substituted —$C_{1-10}$ alkyl, optionally substituted —$C_{2-10}$ alkenyl, optionally substituted aryl, —$C_{1-6}$ alkyl optionally substituted aryl, —C(O)—$(CH_2)_{1-6}$—COOH, —C(O)—$C_{1-6}$ alkyl, —C(O)-optionally substituted aryl, —C(O)—O—$C_{1-6}$ alkyl, or —C(O)—O-optionally substituted aryl. Preferably, the amino terminus protecting group is acetyl, propyl, succinyl, benzyl, benzyloxycarbonyl or t-butyloxycarbonyl.

A protecting group covalently joined to the C-terminal carboxy group reduces the reactivity of the carboxy terminus under in vivo conditions. The carboxy terminus protecting group is preferably attached to the α-carbonyl group of the last amino acid. Carboxy terminus protecting groups include amide, methylamide, and ethylamide.

"Alkyl" refers to a hydrocarbon group of one carbon atom, or a hydrocarbon group joined by carbon-carbon single bonds. The alkyl hydrocarbon group may be straight-chain or contain one or more branches or cyclic groups. Preferably, the alkyl group is 1 to 4 carbons in length. Examples of alkyl include methyl, ethyl, propyl, isopropyl, cyclopropyl, butyl, and t-butyl. The alkyl group may be optionally substituted with one or more substituents selected from the group consisting of halogen (preferably —F or —Cl) —OH, —CN, —SH, —$NH_2$, —$NO_2$, —$C_{1-2}$ alkyl substituted with 1 to 6 halogens (preferably —F or —Cl, more preferably —F), —$CF_3$, —$OCH_3$, or —$OCF_3$.

"Alkenyl" refers to an optionally substituted hydrocarbon group containing one or more carbon-carbon double bonds. The alkenyl hydrocarbon group may be straight-chain or contain one or more branches or cyclic groups. Preferably, the alkenyl group is 2 to 4 carbons in length. The alkenyl group may be optionally substituted with one or more substituents selected from the group consisting of halogen (preferably —F or —Cl), —OH, —CN, —SH, —$NH_2$, —$NO_2$, —$C_{1-2}$ alkyl substituted with 1 to 5 halogens (preferably —F or —Cl, more preferably —F), —$CF_3$, —$OCH_3$, or —$OCF_3$.

"Aryl" refers to an optionally substituted aromatic group with at least one ring having a conjugated pi- electron system, containing up to two conjugated or fused ring systems. Aryl includes carbocyclic aryl, heterocyclic aryl and biaryl groups. Preferably, the aryl is a 5 or 6 membered ring, more preferably benzyl. Aryl substituents are selected from the group consisting of —$C_{1-4}$ alkyl, —$C_{1-4}$ alkoxy, halogen (preferably —F or —Cl), —OH, —CN, —SH, —$NH_2$, —$NO_2$, —$C_{1-2}$ alkyl substituted with 1 to 5 halogens (preferably —F or —Cl, more preferably —F), —$CF_3$, or —$OCF_3$.

A labeled derivative indicates the alteration of a group with a detectable label. Examples of detectable labels include luminescent, enzymatic, and radioactive labels. A preferred radiolabel is $^{125}$I. Labels should be selected and positioned so as not to substantially alter the activity of the MCH antagonist at the MCH receptor. The effect of a particular label on MCH antagonist activity can be determined using assays measuring MCH activity.

In preferred embodiments the optionally modified peptide is a truncated version of Structure I, II, or III corresponding to Structures IV, V, or VI:

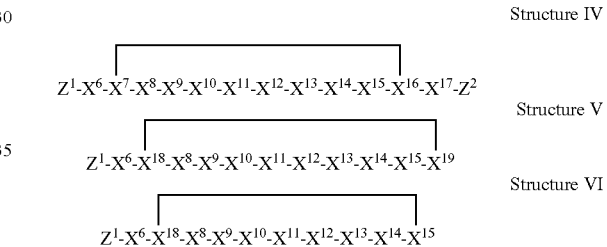

wherein the different groups, and preferred groups, are as described above.

In additional embodiments the peptide has a sequence selected from the group consisting of SEQ. ID. NOs. 11, 12, 13, 14, 16, 18, 19, 20, 21, 25, 27, 29, 30, 32 and 33, a labeled derivative of said peptide or a pharmaceutically acceptable salt of said peptide or of said labeled derivative. Preferred peptides are MCH antagonists shown to have a lower $IC_{50}$ value. Examples of preferred MCH antagonists are provided by SEQ. ID. NOs. 11, 13, 14, 16, 20, 27, 30 and 33.

MCH antagonists can be produced using techniques well known in the art. For example, a polypeptide region of a MCH antagonist can be chemically or biochemically synthesized and, if desired modified to produce a blocked N-terminus and/or blocked C-terminus. Techniques for chemical synthesis of polypeptides are well known in the art. (See e.g., Vincent, in *Peptide and Protein Drug Delivery*, New York, N.Y., Dekker, 1990.) Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook, et al., in *Molecular Cloning, A Laboratory Manual*, $2^{nd}$ Edition, Cold Spring Harbor Laboratory Press, 1989.

Screening for MCH Antagonists

Screening for MCH antagonists is facilitated using a recombinantly expressed MCH receptor. Advantages of using a recombinantly expressed MCH receptor include the ability to express the receptor in a defined cell system so that a response to MCH receptor active compounds can more readily be differentiated from responses to other receptors. For example, an expression vector can be used to introduce an MCH receptor into a cell line such as HEK 293, COS 7, and CHO, wherein the same cell line without the expression vector can act as a control.

Screening for MCH antagonists is facilitated through the use of a MCH agonist in the assay. The use of a MCH agonist in a screening assay provides for MCH receptor activity. The effect of a test compound on such activity can be measured to, for example, evaluate the ability of the compound to inhibit MCH receptor activity.

MCH receptor activity can be measured using different techniques such as detecting a change in the intracellular conformation of the MCH receptor, Gi or Gq activity, and/or intracellular messengers. Gi activity can be measured using techniques well known in the art such as a melonaphore assay, assays measuring cAMP production, inhibition of cAMP accumulation, and binding of $^{35}$S-GTP. cAMP can be measured using different techniques such as a radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button, et al., 1993. *Cell Calcium* 14, 663-671, and Feighner, et al., 1999. *Science* 284, 2184-2188, both of which are hereby incorporated by reference herein.)

Uses of MCH Antagonists

MCH antagonists can be used in methods to achieve a beneficial effect in a subject and for research purposes. Beneficial effects of MCH antagonists include one of more of the following: weight loss, appetite decrease, weight maintenance, cancer (e.g., colon or breast) treatment, pain reduction, stress reduction and/or treatment of sexual dysfunction.

Facilitating weight maintenance or weight loss is particularly useful for overweight and obese patients. Excessive weight is a contributing factor for different diseases including hypertension, diabetes, dyslipidemias, cardiovascular disease, gall stones, osteoarthritis and certain forms of cancers. Bringing about a weight loss can be used, for example, to reduce the likelihood of such diseases and as part of a treatment for such diseases.

Over weight patients include those having a body weight about 10% or more, 20% or more, 30% or more, or 50% or more, than the upper end of a "normal" weight range or Body Mass Index ("BMI"). "Normal" weight ranges are well known in the art and take into account factors such as a patient age, height, and body type.

BMI measures your height/weight ratio. It is determined by calculating weight in kilograms divided by the square of height in meters. The BMI "normal" range is 19-22.

Administration

MCH antagonists can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18$^{th}$ Edition, Ed. Gennaro, Mack Publishing, 1990, and *Modern Pharmaceutics* 2$^{nd}$ Edition, Eds. Banker and Rhodes, Marcel Dekker, Inc., 1990, both of which are hereby incorporated by reference herein.

MCH antagonists can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

MCH antagonists can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

MCH antagonists may also be administered using an intravenous route (both bolus and infusion), an intraperitoneal route, a subcutaneous route, a topical route with or without occlusion, or an intramuscular route. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

MCH antagonists can be provided in kit. Such a kit typically contains an active compound in dosage forms for administration. A dosage form contains a sufficient amount of active compound such that a beneficial effect can be obtained when administered to a patient during regular intervals, such as 1 to 6 times a day, during the course of 1 or more days. Preferably, a kit contains instructions indicating the use of the dosage form for weight reduction (e.g., to treat obesity) or stress reduction, and the amount of dosage form to be taken over a specified time period.

EXAMPLES

Examples are provided below to further illustrate different features of the present invention. The examples also illustrate useful methodology for practicing the invention. These examples do not limit the claimed invention.

Example 1

Synthesis of MCH Antagonists

An example of procedures for producing MCH antagonists is described below. Other procedures for producing and modifying peptides are well known in the art.

Elongation of peptidyl chains on 4-(2',4'-dimethoxyphenyl-Fmoc-aminomethyl)-phenoxy resin and the acetylation of the N-terminal amino groups of the peptides was performed on a 431A ABI peptide synthesizer. Manufacture-supplied protocols were applied for coupling of the hydroxybenzotriazole esters of amino acids in N-methylpyrrolidone (NMP). The fluorenylmethyloxycarbonyl (Fmoc) group was used as a semipermanent alpha-amino protecting group, whereas the side chains protecting groups were: tert-butyl for aspartic acid and tyrosine, 2,2,4,6,7-pentamethyldihydrobenzofuran-5-sulfonyl (Pbf) for arginine, and trityl for cysteine.

Peptides were cleaved from the resin with TFA containing 5% of anisole. After 2 hours at room temperature the resin was filtered, washed with TFA and the combined filtrates were evaporated to dryness in vacuo. The residue was triturated with ether, the precipitate which formed was filtered off, washed with ether, and dried.

Crude peptides were dissolved in 5% acetic acid in water, and the pH of the solutions were adjusted to ca. 8.2 with diluted ammonium hydroxide. The reaction mixtures were stirred vigorously while 0.05% solution of potassium ferricyanide ($K_3Fe(CN)_6$) in water was added dropwise till the reaction mixture remained yellow for about 5 minutes. After an additional 20 minutes oxidation was terminated with ca. 1 ml of acetic acid and the reaction mixtures were lyophilized.

Crude lyophilized peptides were analyzed by analytical reverse-phase high-pressure liquid chromatography (RP HPLC) on a C18 Vydac column attached to a Waters 600E system with automatic Wisp 712 injector and 991 Photodiode Array detector. A standard gradient system of 0-100% buffer B in 30 minutes was used for analysis: buffer A was 0.1% trifluoroacetic acid in water and buffer B was 0.1% trifluoroacetic acid in acetonitrile. HPLC profiles were recorded at 210 nm and 280 nm. Preparative separations were performed on a Waters Delta Prep 4000 system with a semipreparative C18 RP Waters column. The above-described solvent system of water and acetonitrile, in a gradient of 20-80% buffer B in 60 minutes, was used for separation. The chromatographically homogenous compounds were analyzed by electrospray mass spectrometry.

Example 2

Aequorin Bioluminescence Functional Assay

The aequorin bioluminescence assay can be used to measure the activity of G protein-coupled receptors that couple through the Gα protein subunit family consisting of Gq and G11. Such coupling leads to phospholipase C activation, intracellular calcium mobilization and protein kinase C activation.

Measurement of rat MCH-1R and human MCH-2R receptor activity was preformed using stable cell lines expressing these receptors in the aequorin-expressing stable reporter cell line 293-AEQ17 (Button et al., Cell Calcium 14:663-671, 1993). The apo-aequorin in the cells was charged for 1 hour with coelenterazine (10 μM) under reducing conditions (300 μM reduced glutathione) in ECB buffer (140 mM NaCl, 20 mM KCl, 20 mM HEPES-NaOH [pH=7.4], 5 mM glucose, 1 mM $MgCl_2$, 1 mM $CaCl_2$, 0.1 mg/ml bovine serum albumin).

The cells were harvested, washed once in ECB buffer and resuspended to 500,000 cells/ml. 100 μl of cell suspension (corresponding to $5 \times 10^4$ cells) was then injected into the test plate containing MCH or test compounds, and the integrated light emission was recorded over 30 seconds, in 0.5 second units. 20 μL of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton X-100 lysis response.

Example 3

Binding Assay

Binding to human MCH-1R or human MCH-2R was assayed by measuring the ability of a compound to inhibit binding of [$^{125}$I]-human MCH (phe$^{13}$, Tyr$^{19}$ substituted) to membranes prepared from cells stably expressing the MCH-1R or MCH-2R receptor. Human MCH (Phe$^{13}$, Tyr$^{19}$ substituted) used in the assay was radiolabeled with $^{125}$I at $_{19}$Tyr to a specific activity of ~2000 Ci/mmol (NEN Life Science Products, Boston, Mass.).

Cell membranes were prepared on ice. Each T-75 flask was rinsed twice with 10 ml of Enzyme-free Cell Dissociation Buffer (Specialty Media, Lavallette, N.J.), and the cell monolayer was detached in an additional 10 ml of Enzyme-free Cell Dissociation Buffer by incubation at room temperature for 10 minutes. Dissociated cells were centrifuged (500×g for 10 minutes at 4° C.), resuspended in 5 ml homogenization buffer (10 mM Tris-HCl, pH 7.4, 0.01 mM Pefabloc, 10 μM phosphoramidon, 40 μg/ml bacitracin) and then homogenized using a glass homogenizer (10-15 strokes). The homogenate was centrifuged for 10 minutes (1,000×g at 4° C.). The resulting supernatant was then centrifuged at 38,700×g for 15 minutes at 4° C. Pelleted membranes were resuspended (passed through 25 gauge needle 5 times), snap-frozen on liquid nitrogen, and stored at −80° C. until use.

Binding was performed in a 96-well filter assay or Scintillation Proximity Assay (SPA)-based format using cell membranes from a stable CHO or HEK-293 cell line expressing MCH-1R or MCH-2R. For the filter assay, reactions were performed at 20° C. for 1 hour in a total volume of 0.2 ml containing: 0.05 ml of membrane suspension (~3 μg protein), 0.02 ml of [$^{125}$I]-human MCH (Phe$^{13}$, Tyr$^{19}$ substituted; 30 pM), 0.01 ml of competitor and 0.12 ml of binding buffer (50 mM Tris-HCl, pH 7.4, 10 mM $MgCl_2$, 2 mM EDTA, 200 μg/ml bacitracin, 1 μM phosphoramidon).

Bound radioligand was separated by rapid vacuum filtration (Packard Filtermate 96-well cell harvester) through GF/C filters pretreated for 1 hour with 1% polyethylenimine.

After application of the membrane suspension to the filter, the filters were washed 3 times with 3 ml each of ice-cold 50 mM Tris-HCl, pH 7.4, 10 mM $MgCl_2$, 2 mM EDTA, 0.04% Tween 20 and the bound radioactivity on the filters was quantitated by scintillation counting (TopCount device). Specific binding (>80% of total) is defined as the difference between total binding and non-specific binding conducted in the presence of 100 nM unlabeled human MCH.

For the SPA-based assay, WGA-PVT beads (NEN Life Sciences Products) were resuspended in Dulbecco's PBS with calcium and magnesium (500 mg beads in 4 ml PBS). For each 96-well assay plate, 0.18 ml of beads was pre-coated with an MCH receptor by mixing with 0.2 ml MCH receptor CHO cell membranes (~0.2-4 mg protein) and 1.5 ml SPA assay buffer (50 mM Tris-HCl, pH 7.4, 10 mM $MgCl_2$, 2 mM EDTA, 0.1% BSA, 12% glycerol). The suspension was mixed gently for 20 minutes, 12.3 ml of assay buffer and protease inhibitors were added (final concentration given): 2 µg/ml leupeptin, 10 µM phosphoramidon, 40 µg/ml bacitracin, 5 µg/ml aprotinin, 0.1 mM Pefabloc.

Coated beads were kept on ice until use. For each well, 0.145 ml of beads were added to Optiplate assay plates (Packard 6005190), followed by 0.002-0.004 ml of competitor and 0.05 ml of [$^{125}I$]-human MCH ($Phe^{13}$, $Tyr^{19}$ substituted; 30 pM). Binding reactions were allowed to proceed at room temperature for 3 hours. Quantitation was performed by scintillation counting (TopCount device).

Example 4

Antagonist Assay

The ability of a compound to act as an MCH antagonist was evaluated using the aequorin-expressing stable reporter cell line 293-AEQ17 expressing the rat MCH-1R. Cells were grown in DMEM (high glucose) supplemented with 10% FBS (Hyclone), 500 µg/ml G418, 200 µg/ml hygromycin and 25 mM HEPES in T75 flasks.

The assay itself involved charging apoaequorin with coelenterazine cp(Molecular Probes, C-14260) and was performed as follows:

1. Confluent T75 flasks are rinsed 1× with 12 ml Hams F12 medium+300 µM glutathione+0.1% FBS.

2. The cells were charged by adding 8 ml Hams F12+0.1% FBS+300 µM glutathione+10 µM coelenterazine, incubate at 37° C. for 1 hour.

3. T75 flasks are rinsed with 6 ml ECB (140 mM NaCl, 20 mM KCl, 20 mM HEPES, 5 mM glucose, 1 mM $MgCl_2$, 1 mM $CaCl_2$, 0.1 mg/ml BSA, pH 7.3 to 7.4).

4. ECB (6 ml) is added to the flask and the cells are dissociated with a rubber-tipped scraper, centrifuged for 5 minutes at 2500 rpm and the cell pellet resuspended in 5 ml ECB. The cells are counted and diluted to $5×10^5$/ml.

5. The $EC_{50}$ at the rat MCH-1R is determined using the Luminoscan RT luminometer by injecting 50,000 cells/0.1 ml into a 96 well plate containing 0.1 ml of 2× ligand concentration.

6. Antagonist activity of compounds exhibiting an $IC_{50}$<1000 nM in the binding assay are determined by preincubating 50,000/0.1 ml charged cells with compound for 10 minutes and then initiating the reaction by injecting 0.1 ml of 2× $EC_{50}$ concentration of MCH.

Example 5

MCH Activity

The activity of different test compounds at MCH-1R and MCH-2R is shown in Table 1. Binding and agonist activity at the MCH-1R and MCH-2R was determined as described in Examples 2 and 3. Antagonist $IC_{50}$ was determined as described in Example 4. $K_b$ was determined using the procedures described in *Trends in Pharmacol. Sci.* 14:237-239, 1993.

Structures for compounds 2-36 are provided in Table 1 by modifying the structure at the top of the table as indicated in the table. Human MCH has the following structure ("*" indicates cyclization (S-S)):

```
              *                                           *    (SEQ. ID. NO. 1)
Asp-Phe-Asp-Met-Leu-Arg-Cys-Met-Leu-Gly-Arg-Val-Tyr-Arg-Pro-Cys-
Trp-Gln-Val
```

TABLE 1

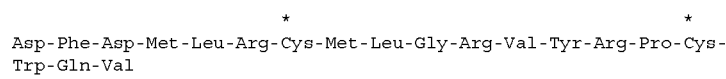

Ac-$Arg^6$-$Cys^7$-$Met^8$-$Leu^9$-$Gly^{10}$-$Arg^{11}$-$Val^{12}$-$Tyr^{13}$-$Arg^{14}$-$Pro^{15}$-$Cys^{16}$-$NH_2$

| | | MCH-1R | | | | MCH-2R | | |
|---|---|---|---|---|---|---|---|---|
| | | Binding | Agonist | | Antagonist | Binding | Agonist | |
| SEQ. ID. NO. | Compound | $IC_{50}$ (nM) | $EC_{50}$ (nM) | Activation % | $IC_{50}$ (nM) $K_b$ (nM) | $IC_{50}$ (nM) | $EC_{50}$ (nM) | Activation % |
| 1 | hMCH | 0.3 | 30.9 | 100 | | 0.5 | 30.7 | 100 |
| 2 | | 1.4 | 20 | 99 | | 2 | 6.2 | 98 |
| 3 | $Ava^{9,10}$ | 3.7 | 587 | 82 | | 350 | >10000 | |
| 4 | $D-Arg^6$, $Ava^{9,10}$ | 3.7 | 1080 | 72 | | 5% @ 1 | >10000 | 7 |
| 5 | $Gva^6$, $Ava^{9,10}$ | 6.3 | 380 | 10 | | | >10000 | 31 |
| 6 | $Gva^6$, $Ava^{9,10}$, $ΔArg^{14}$, $Gly^{15}$ | >1000 | >10000 | | 0.1 | 28% @ 10 | >10000 | 25 |
| 7 | $Aoct^{8,9,10}$ | >1000 | >10000 | | 0.1 | 51% @ 10 | 1040 | 27 |
| 8 | $Ava^{14,15}$ | 6.6 | 406 | 75 | | 6% @ 2 | >10000 | |
| 9 | $Δ(Ac-Arg^6)$, $Ava^{14,15}$ | 550 | | | | 40% @ 10 | | |
| 10 | $D-Arg^6$, $Ava^{14,15}$ | 19.5 | 1300 | 28 | | 41% @ 4 | >10000 | 18 |

TABLE 1-continued

Ac-Arg$^6$-Cys$^7$-Met$^8$-Leu$^9$-Gly$^{10}$-Arg$^{11}$-Val$^{12}$-Tyr$^{13}$-Arg$^{14}$-Pro$^{15}$-Cys$^{16}$-NH$_2$

| | | MCH-1R | | | | | MCH-2R | | |
|---|---|---|---|---|---|---|---|---|---|
| | | Binding | Agonist | | Antagonist | | Binding | Agonist | |
| SEQ. ID. NO. | Compound | IC$_{50}$ (nM) | EC$_{50}$ (nM) | Activation % | IC$_{50}$ (nM) | K$_b$ (nM) | IC$_{50}$ (nM) | EC$_{50}$ (nM) | Activation % |
| 11 | Gva$^6$, Ava$^{14,15}$ | 3 | >10000 | 3 | 2.9 | 1.25 | 55% 10 | >10000 | 91 |
| 12 | Gbu$^6$, Ava$^{14,15}$ | 8 | >10000 | 6 | | | 4000 | >10000 | 14 |
| 13 | Gva$^6$, γAbu$^{14,15}$ | 49 | >10000 | 3.5 | 6.84 | 3 | 29% @ 10 | >10000 | 35 |
| 14 | Gva$^6$, β-Ala$^{14,15}$ | 176 | >10000 | 3.6 | 6.8 | 3 | 43% @ 10 | >10000 | 32 |
| 15 | Gva$^6$, Gly$^{14,15}$ | 920 | >10000 | 3 | | | | >10000 | 6 |
| 16 | Gva$^6$, Nle$^8$, Ava$^{14,15}$ | 11 | >10000 | 3 | 13.8 | 6 | 79% @ 10 | >10000 | 59 |
| 17 | Gva$^6$, αAbu$^8$, Ava$^{14,15}$ | 830 | >10000 | 3 | | | | >10000 | 7 |
| 18 | Gva$^6$, Ava$^{14,15}$, OH | 290 | >10000 | 3.8 | 75.7 | 32.9 | 0% @ 10 | >10000 | 38 |
| 19 | Gva$^6$, Ala$^8$, Ava$^{14,15}$ | 140 | >10000 | | 67 | 29 | | >10000 | 45 |
| 20 | Gva$^6$, Ala$^{12}$, Ava$^{14,15}$ | 29 | >10000 | 3.4 | 4.7 | 2 | 23% @ 10 | >10000 | 38 |
| 21 | ΔArg$^6$, Ava$^{14,15}$ | 180 | >10000 | 3 | | | 5% @ 1 | 1100 | 6 |
| 22 | Ala$^8$, Ava$^{14,15}$ | >1000 | >10000 | 0.1 | | | 44% @ 10 | 1830 | 25 |
| 23 | Gva$^6$, ΔLeu$^9$, Ava$^{14,15}$ | >1000 | >10000 | 0.1 | | | | >10000 | 26 |
| 24 | D-Cys$^7$, Ava$^{14,15}$ | 350 | >10000 | 3 | | | 50% @ 10 | >10000 | 17 |
| 25 | Gva$^6$, D-Cys$^7$, Ava$^{14,15}$ | 66 | >10000r | 0.1 | | | 61% @ 10 | >10000 | 25 |
| 26 | D-Nle$^{10}$, Ava$^{14,15}$ | 223 | 544 | 43 | | | 64% @ 10 | >10000 | 91 |
| 27 | Gva$^6$, D-Nle$^{10}$, Ava$^{14,15}$ | 28 | >10000 | 3 | 5.4 | 2.4 | 62% @ 10 | >10000 | 91 |
| 28 | D-Pro$^{10}$, Ava$^{14,15}$ | 700 | | | | | 5% @ 1 | >10000 | 7 |
| 29 | Gva$^6$, CisAcx$^{14,15}$ | 17 | >10000 | | | | 3000 | | |
| 30 | Ava$^{9,10}$, Ava$^{14,15}$ | 88 | >10000 | 3 | 10.6 | 4.6 | 10% @ 1 | >10000 | 16 |
| 31 | β-Ala$^{9,10}$, β-Ala$^{14,15}$ | 76% @ 10 | >10000 | 3 | | | | >10000 | 6 |
| 32 | Gva$^6$, Ava$^{9,10}$, Ava$^{14,15}$ | 62 | >10000 | 3 | 56 | 24 | 49% @ 10 | >10000 | 91 |
| 33 | D-Arg$^6$, Ava$^{9,10}$, Ava$^{14,15}$ | 135 | >10000 | 2 | 13.8 | 6 | 38% @ 10 | >10000 | 28 |
| 34 | Gva$^6$, Ala$^8$, Ala$^{12}$, Ava$^{9,10}$, Ava$^{14,15}$, acid | >1000 | >10000 | 0.1 | | | 36% @ 10 | >10000 | 28 |
| 35 | Gva$^6$, Nle$^8$, Ala$^{12}$, Ava$^{9,10}$, Ava$^{14,15}$, acid | >1000 | >10000 | 0.1 | | | 40% @ 10 | >10000 | 25 |
| 36 | Gva$^6$, Ava$^{8,9,10}$, Ava$^{14,15}$ | >1000 | >10000 | 0.1 | | | 34% @ 10 | >10000 | 24 |

"Ava" refers to 5-aminovaleric acid,
"Gbu" refers to 4-guanidinobutyric acid,
"Aoct" refers to 8-aminooctanoic acid,
"cisAcx" refers to cis-4-amino-1-cyclohexanecarboxylic acid,
"α-Abu" refers to α-aminobutyric acid,
"γ-Abu" refers to γ-aminobutyric acid, and
"Gva" refers to des-amino-arginine (also known as 5-guanidino-valeric acid).
Reference to "OH" or "acid" indicates the presence of a C-terminal carboxyl group.

Other embodiments are within the following claims. While several embodiments have been shown and described, various modifications may be made without departing from the spirit and scope of the present invention.

What is claimed is:

1. An optionally labeled peptide having the structure:

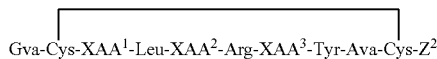

Gva-Cys-XAA$^1$-Leu-XAA$^2$-Arg-XAA$^3$-Tyr-Ava-Cys-Z$^2$ wherein Gva is des-amino-arginine
XAA$^1$ is either methionine or norleucine;
XAA$^2$ is either glycine or D-norleucine;
XAA$^3$ is valine or alanine;
Ava is 5-aminovaleric acid; and
Z$^2$ is an optionally present protecting group that, if present, is covalently joined to the C-terminal carboxy group;
or a pharmaceutically acceptable salt of said peptide;
wherein said peptide is optionally labeled with a detectable label selected from the group consisting of: luminescent, enzymatic and radioactive.

2. The peptide of claim 1, where said peptide consists of the structure:

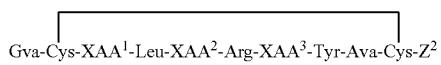

Gva-Cys-XAA$^1$-Leu-XAA$^2$-Arg-XAA$^3$-Tyr-Ava-Cys-Z$^2$ wherein Gva is des-amino-arginine;
XAA$^1$ is either methionine or norleucine;
XAA$^2$ is either glycine or D-norleucine;
XAA$^3$ is valine or alanine;
Ava is 5-aminovaleric acid; and
Z$^2$ is an optionally present protecting group that, if present, is covalently joined to the C-terminal carboxy group;
or a pharmaceutically acceptable salt of said peptide;
wherein said peptide is optionally labeled with a detectable label selected from the group consisting of: luminescent, enzymatic and radioactive.

3. The peptide of claim 2, wherein Z$^2$ is —NH$_2$.

4. The peptide of claim 1, wherein said peptide is either SEQ ID NO: 11, SEQ ID NO: 16, SEQ ID NO: 20, SEQ ID NO: 27, or a pharmaceutically acceptable salt thereof.

5. The peptide of claim 4, wherein said peptide is either SEQ ID NO: 11, SEQ ID NO: 27 or a pharmaceutically acceptable salt thereof.

6. A method of inhibiting MCH-1R activity in a subject comprising the step of administering to said subject an effective amount of a peptide consisting of the structure:

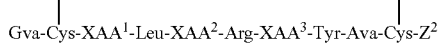

Gva-Cys-XAA$^1$-Leu-XAA$^2$-Arg-XAA$^3$-Tyr-Ava-Cys-Z$^2$ wherein Gva is des-amino arginine;
XAA$^1$ is either methionine or norleucine;
XAA$^2$ is either or D-norleucine;
XAA$^3$ is valine or alanine;
Ava is 5-aminovaleric acid; and
Z$^2$ is an optionally present protecting group that, if present, is covalently joined to the C-terminal carboxy group;
or a pharmaceutically acceptable salt of said peptide.

7. The method of claim 6, wherein Z$^2$ is —NH$_2$.

8. The method of claim 6, wherein said peptide is either SEQ ID NO: 11, SEQ ID NO: 16, SEQ ID NO: 20, SEQ ID NO: 27, or a pharmaceutically acceptable salt thereof.

9. The method of claim 6, wherein said peptide is either SEQ ID NO: 11, SEQ ID NO: 27 or a pharmaceutically acceptable salt thereof.

10. A method of treating a subject to achieve a weight loss or to maintain weight comprising the step of administering to said subject an effective amount of a peptide consisting of the structure;

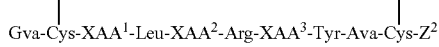

Gva-Cys-XAA$^1$-Leu-XAA$^2$-Arg-XAA$^3$-Tyr-Ava-Cys-Z$^2$ wherein Gva is des-amino arginine;
XAA$^1$ is either methionine or norleucine;
XAA$^2$ is either glycine or D-norleucine;
XAA$^3$ is valine or alanine;
Ava is 5-aminovaleric acid; and
Z$^2$ is an optionally present protecting group that, if present, is covalently joined to the C-terminal carboxy group;
or a pharmaceutically acceptable salt of said peptide.

11. The method of claim 10, wherein said method causes a weight loss.

12. The method of claim 10 wherein $Z^2$ is —NH$_2$.

13. The method of claim 10, wherein said peptide is either SEQ ID NO: 11, SEQ ID NO: 16, SEQ ID NO: 20, SEQ ID NO: 27, or a pharmaceutically acceptable salt thereof.

14. The method of claim 10, wherein said peptide is either SEQ ID NO: 11, SEQ ID NO: 27 or a pharmaceutically acceptable salt thereof.

* * * * *

SEQUENCE LISTING

<160> NUMBER OF SEQ ID NOS: 36

<210> SEQ ID NO 1
<211> LENGTH: 19
<212> TYPE: PRT
<213> ORGANISM: Human
<220> FEATURE:
<221> NAME/KEY: DISULFID
<222> LOCATION: (7)...(16)

<400> SEQUENCE: 1

Asp Phe Asp Met Leu Arg Cys Met Leu Gly Arg Val Tyr Arg Pro Cys
1               5                   10                  15

Trp Gln Val

<210> SEQ ID NO 2
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 2

Arg Cys Met Leu Gly Arg Val Tyr Arg Pro Cys
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (4)...(5)
<223> OTHER INFORMATION: Xaa = 5-aminovaleric acid

<400> SEQUENCE: 3

Arg Cys Met Xaa Xaa Arg Val Tyr Arg Pro Cys
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: MOD_RES
<222> LOCATION: (4)...(5)
<223> OTHER INFORMATION: Xaa = 5-aminovaleric acid

<400> SEQUENCE: 4

Xaa Cys Met Xaa Xaa Arg Val Tyr Arg Pro Cys
 1               5                  10

```
<210> SEQ ID NO 5
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (4)...(5)
<223> OTHER INFORMATION: Xaa = 5-aminovaleric acid

<400> SEQUENCE: 5

Xaa Cys Met Xaa Xaa Arg Val Tyr Arg Pro Cys
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(10)
<220> FEATURE:
<221> NAME/KEY: ACETYLATION
<222> LOCATION: (1)...(1)
<220> FEATURE:
<221> NAME/KEY: AMIDATION
<222> LOCATION: (10)...(10)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (4)...(5)
<223> OTHER INFORMATION: Xaa = 5-aminovaleric acid

<400> SEQUENCE: 6

Xaa Cys Met Xaa Xaa Arg Val Tyr Gly Cys
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (3)...(5)
<223> OTHER INFORMATION: Xaa = 8-aminoactanoic acid
```

```
<400> SEQUENCE: 7

Arg Cys Xaa Xaa Xaa Arg Val Tyr Arg Pro Cys
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (9)...(10)
<223> OTHER INFORMATION: Xaa = 5-aminovaleric acid

<400> SEQUENCE: 8

Arg Cys Met Leu Gly Arg Val Tyr Xaa Xaa Cys
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (1)...(10)
<220> FEATURE:
<221> NAME/KEY: AMIDATION
<222> LOCATION: (10)...(10)
<220> FEATURE:
<221> NAME/KEY: MOD_RES
<222> LOCATION: (8)...(9)
<223> OTHER INFORMATION: Xaa = 5-aminovaleric acid

<400> SEQUENCE: 9

Cys Met Leu Gly Arg Val Tyr Xaa Xaa Cys
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: MOD_RES
<222> LOCATION: (9)...(10)
<223> OTHER INFORMATION: Xaa = 5-aminovaleric acid
```

```
<400> SEQUENCE: 10

Xaa Cys Met Leu Gly Arg Val Tyr Xaa Xaa Cys
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (9)...(10)
<223> OTHER INFORMATION: Xaa = 5-aminovaleric acid

<400> SEQUENCE: 11

Xaa Cys Met Leu Gly Arg Val Tyr Xaa Xaa Cys
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = 4-guanidinobutyric acid
<220> FEATURE:
<221> NAME/KEY: MOD_RES
<222> LOCATION: (9)...(10)
<223> OTHER INFORMATION: Xaa = 5-aminovaleric acid

<400> SEQUENCE: 12

Xaa Cys Met Leu Gly Arg Val Tyr Xaa Xaa Cys
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
```

```
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (9)...(10)
<223> OTHER INFORMATION: Xaa = gamma-aminobutyric acid

<400> SEQUENCE: 13

Xaa Cys Met Leu Gly Arg Val Tyr Xaa Xaa Cys
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (9)...(10)
<223> OTHER INFORMATION: Xaa = beta-alanine

<400> SEQUENCE: 14

Xaa Cys Met Leu Gly Arg Val Tyr Xaa Xaa Cys
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine

<400> SEQUENCE: 15

Xaa Cys Met Leu Gly Arg Val Tyr Gly Gly Cys
 1               5                  10

<210> SEQ ID NO 16
<211> LENGTH: 11
<212> TYPE: PRT
<213> ORGANISM: Artificial Sequence
```

```
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (3)...(3)
<223> OTHER INFORMATION: Xaa - Norleucine

<400> SEQUENCE: 16

Xaa Cys Xaa Leu Gly Arg Val Tyr Xaa Xaa Cys
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (3)...(3)
<223> OTHER INFORMATION: Xaa = alpha-aminobutyric acid
<220> FEATURE:
<221> NAME/KEY: MOD_RES
<222> LOCATION: (9)...(10)
<223> OTHER INFORMATION: Xaa = 5-aminovaleric acid

<400> SEQUENCE: 17

Xaa Cys Xaa Leu Gly Arg Val Tyr Xaa Xaa Cys
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: MOD_RES
<222> LOCATION: (1)...(1)
<223> OTHER INFORMATION: Xaa = des-amino-arginine
```

```
<220> FEATURE:
<221> NAME/KEY: MOD_RES
<222> LOCATION: (9)...(10)
<223> OTHER INFORMATION: Xaa = 5-aminovaleric acid

<400> SEQUENCE: 18

Xaa Cys Met Leu Gly Arg Val Tyr Xaa Xaa Cys
 1               5                  10

<210> SEQ ID NO 19
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (9)...(10)
<223> OTHER INFORMATION: Xaa = 5-aminovaleric acid

<400> SEQUENCE: 19

Xaa Cys Ala Leu Gly Arg Val Tyr Xaa Xaa Cys
 1               5                  10

<210> SEQ ID NO 20
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (9)...(10)
<223> OTHER INFORMATION: Xaa = 5-aminovaleric acid

<400> SEQUENCE: 20

Xaa Cys Met Leu Gly Arg Ala Tyr Xaa Xaa Cys
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: MCH Antagonists
```

```
<220> FEATURE:
<221> NAME/KEY: DISULFID
<222> LOCATION: (1)...(10)
<220> FEATURE:
<221> NAME/KEY: AMIDATION
<222> LOCATION: (10)...(10)
<220> FEATURE:
<221> NAME/KEY: MOD_RES
<222> LOCATION: (8)...(9)
<223> OTHER INFORMATION: Xaa = 5-aminovaleric acid

<400> SEQUENCE: 21

Cys Met Leu Gly Arg Val Tyr Xaa Xaa Cys
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (9)...(10)
<223> OTHER INFORMATION: Xaa = 5-aminovaleric acid

<400> SEQUENCE: 22

Arg Cys Ala Leu Gly Arg Val Tyr Xaa Xaa Cys
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(10)
<220> FEATURE:
<221> NAME/KEY: ACETYLATION
<222> LOCATION: (1)...(1)
<220> FEATURE:
<221> NAME/KEY: AMIDATION
<222> LOCATION: (10)...(10)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (8)...(9)
<223> OTHER INFORMATION: Xaa = 5-aminovaleric acid

<400> SEQUENCE: 23

Xaa Cys Met Gly Arg Val Tyr Xaa Xaa Cys
 1               5                  10

<210> SEQ ID NO 24
<211> LENGTH: 11
<212> TYPE: PRT
<213> ORGANISM: Artificial Sequence
```

```
<220> FEATURE:
<223> OTHER INFORMATION: MCH Antagonists
<220> FEATURE:
<221> NAME/KEY: DISULFID
<222> LOCATION: (2)

```
<220> FEATURE:
<221> NAME/KEY: MOD_RES
<222> LOCATION: (9)...(10)
<223> OTHER INFORMATION: Xaa = 5-aminovaleric acid

<400> SEQUENCE: 26

Arg Cys Met Leu Xaa Arg Val Tyr Xaa Xaa Cys
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (5)...(5)
<223> OTHER INFORMATION: Xaa = D-norleucine
<220> FEATURE:
<221> NAME/KEY: MOD_RES
<222> LOCATION: (9)...(10)
<223> OTHER INFORMATION: Xaa = 5-aminovaleric acid

<400> SEQUENCE: 27

Xaa Cys Met Leu Xaa Arg Val Tyr Xaa Xaa Cys
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa - D-proline
<220> FEATURE:
<221> NAME/KEY: MOD_RES
<222> LOCATION: (9)...(10)
<223> OTHER INFORMATION: Xaa = 5-aminovaleric acid

<400> SEQUENCE: 28

Arg Cys Met Leu Xaa Arg Val Tyr Xaa Xaa Cys
 1               5                  10

<210> SEQ ID NO 29
<211> LENGTH: 11
<212> TYPE: PRT
<213> ORGANISM: Artificial Sequence
```

```
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (9)...(10)
<223> OTHER INFORMATION: Xaa = cis-4-amino-1-cyclohexanecarboxylic acid

<400> SEQUENCE: 29

Xaa Cys Met Leu Gly Arg Val Tyr Xaa Xaa Cys
 1               5                  10

<210> SEQ ID NO 30
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (4)...(5)
<223> OTHER INFORMATION: Xaa = 5-aminovaleric acid
<220> FEATURE:
<221> NAME/KEY: MOD_RES
<222> LOCATION: (9)...(10)
<223> OTHER INFORMATION: Xaa = 5-aminovaleric acid

<400> SEQUENCE: 30

Arg Cys Met Xaa Xaa Arg Val Tyr Xaa Xaa Cys
 1               5                  10

<210> SEQ ID NO 31
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (4)...(5)
<223> OTHER INFORMATION: Xaa = B-alanine
<220> FEATURE:
<221> NAME/KEY: MOD_RES
<222> LOCATION: (9)...(10)
<223> OTHER INFORMATION: Xaa = B-alanine
```

-continued

```
<400> SEQUENCE: 31

Arg Cys Met Xaa Xaa Arg Val Tyr Xaa Xaa Cys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (4)...(5)
<223> OTHER INFORMATION: Xaa = 5-aminovaleric acid
<220> FEATURE:
<221> NAME/KEY: MOD_RES
<222> LOCATION: (9)...(10)
<223> OTHER INFORMATION: Xaa = 5-aminovaleric acid

<400> SEQUENCE: 32

Xaa Cys Met Xaa Xaa Arg Val Tyr Xaa Xaa Cys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: MCH Antagonists
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: MOD_RES
<222> LOCATION: (4)...(5)
<223> OTHER INFORMATION: Xaa = 5-aminovaleric acid
<220> FEATURE:
<221> NAME/KEY: MOD_RES
<222> LOCATION: (9)...(10)
<223> OTHER INFORMATION: Xaa = 5-aminovaleric acid

<400> SEQUENCE: 33

Xaa Cys Met Xaa Xaa Arg Val Tyr Xaa Xaa Cys
1               5                   10

<210> SEQ ID NO 34
<211> LENGTH: 11
<212> TYPE: PRT
<213> ORGANISM: Artificial Sequence
```

```
<220> FEATURE:
<223> OTHER INFORMATION: MCH Antagonists
<220> FEATURE:
<221> NAME/KEY: DISULFID
<222> LOCATION: (2

```
-continued
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: MOD_RES
<222> LOCATION: (3)...(5)
<223> OTHER INFORMATION: Xaa = 5-aminovaleric acid
<220> FEATURE:
<221> NAME/KEY: MOD_RES
<222> LOCATION: (9)...(10)
<223> OTHER INFORMATION: Xaa = 5-aminovaleric acid

<400> SEQUENCE: 36

Xaa Cys Xaa Xaa Xaa Arg Val Tyr Xaa Xaa Cys
 1               5                   10
```